(12) United States Patent
Farnham et al.

(10) Patent No.: US 7,696,292 B2
(45) Date of Patent: Apr. 13, 2010

(54) LOW-POLYDISPERSITY PHOTOIMAGEABLE ACRYLIC POLYMERS, PHOTORESISTS AND PROCESSES FOR MICROLITHOGRAPHY

(75) Inventors: William Brown Farnham, Hockessin, DE (US); Michael Fryd, Philadelphia, PA (US); Frank Leonard Schadt, III, Wilmington, DE (US)

(73) Assignee: Commonwealth Scientific and Industrial Research Organisation, Act (AU)

( * ) Notice: Subject to any disclaimer, the term of this patent is extended or adjusted under 35 U.S.C. 154(b) by 1059 days.

(21) Appl. No.: 10/943,063

(22) Filed: Sep. 16, 2004

(65) Prior Publication Data

US 2005/0119378 A1 Jun. 2, 2005

Related U.S. Application Data

(60) Provisional application No. 60/505,038, filed on Sep. 22, 2003.

(51) Int. Cl.
*C08F 20/00* (2006.01)
*C08F 2/00* (2006.01)
*G03C 1/00* (2006.01)

(52) U.S. Cl. ............... 526/319; 526/317.1; 526/280; 526/281; 526/318; 526/222; 430/270.1; 430/325; 430/326; 430/907

(58) Field of Classification Search ............ 526/317.1, 526/318, 280, 281, 319; 430/270.1, 325, 430/326, 907
See application file for complete search history.

(56) References Cited

U.S. PATENT DOCUMENTS

| | | | | |
|---|---|---|---|---|
| 5,109,088 A | * | 4/1992 | Ohwada et al. | ............ 526/273 |
| 5,585,222 A | * | 12/1996 | Kaimoto et al. | ............ 430/296 |
| 6,200,725 B1 | | 3/2001 | Takechi et al. | |
| 6,280,898 B1 | | 8/2001 | Hasegawa et al. | |
| 6,441,115 B1 | | 8/2002 | Chang et al. | |
| 6,512,081 B1 | | 1/2003 | Rizzardo et al. | |
| 6,784,312 B2 | | 8/2004 | Miyazawa et al. | |
| 6,790,587 B1 | * | 9/2004 | Feiring et al. | ............ 430/270.1 |
| 6,953,649 B2 | | 10/2005 | Prat et al. | |
| 7,510,817 B2 | | 3/2009 | Benoit et al. | |
| 2004/0242798 A1 | | 12/2004 | Sounik et al. | |
| 2004/0248039 A1 | | 12/2004 | Sounik et al. | |
| 2005/0112495 A1 | | 5/2005 | Feiring et al. | |
| 2006/0247400 A1 | | 11/2006 | Sounik et al. | |

FOREIGN PATENT DOCUMENTS

| | | |
|---|---|---|
| EP | 0 825 247 A2 | 2/1998 |
| EP | 1 103 856 A1 | 5/2001 |
| EP | 0 910 587 B1 | 12/2001 |
| WO | WO 98/01478 | 1/1998 |
| WO | WO 99/31144 | 6/1999 |
| WO | WO 00/66575 A2 | 11/2000 |
| WO | WO 01/95034 A1 | 12/2001 |
| WO | WO 03/075094 A1 | 9/2003 |
| WO | WO 03/077029 A1 | 9/2003 |
| WO | WO 2005/000923 A1 | 1/2005 |
| WO | WO 2005/000924 A1 | 1/2005 |
| WO | WO 2005/003192 A1 | 1/2005 |
| WO | WO 2005/003198 A1 | 1/2005 |
| WO | WO 2005/101124 A1 | 10/2005 |
| WO | WO 2005/108458 A1 | 11/2005 |

OTHER PUBLICATIONS

J.A. Delaire et al. "Effects of molecular weights and polydispersity on the properties of poly(trifluoroethylmethacrylate) as a positive x ray and electron resist", Journal of Vacuum Science & Technology B 8, Jan./Feb. 1990, No. 1, New York, USA, pp. 32-38.*

Ting-Yu Lee et al. "Polymers with well controlled mmolecular weight for DUV/VUV lithography", Advances in Resist Technology and Processing XX, Proceeding of SPEI, vol. 5039 (2003), pp. 548-557.*

Ting-Yu Lee et al. "Polymers with well controlled molecular weight for DUVNUV lithography", Advances in Resist Technology and Processing XX, Proceeding of SPEI, vol. 5039 (2003), pp. 548-557.*

T.-Y Lee et al., Advances in Resist Technology and Processing XX, Theodore H. Fedynyshyn, Editor, Proceedings of SPIE, vol. 5039:548-557, 2003.

Moad and Solomon, The Chemistry of Free Radical Polymerization, Pergamon, London, 1995, pp. 53-95.

Theodore H. Fedynyshyn, et al., "Prospects for Using Existing Resists for Evaluating 157-nm Imaging Systems", *Proc. of SPIE* vol. 3999, pp. 335-346.

Daniel P. Sanders, et al., "Fluoroalcohol Materials With Tailored Interfacial Properties for Immersion Lithography", *Proc. of SPIE* vol. 6519, pp. 651904-1 to 651904-12, (2007).

* cited by examiner

*Primary Examiner*—David Wu
*Assistant Examiner*—Michael M Bernshteyn

(57) ABSTRACT

The invention pertains to low polydispersity acrylic polymers useful for photoimaging and photoresist compositions, and to the photoimaging processes which use these compositions. The low polydispersity polymers of this invention are prepared using controlled radical polymerization (CRP) techniques, such as RAFT (reversible addition fragmentation chain transfer) polymerization.

5 Claims, No Drawings

LOW-POLYDISPERSITY PHOTOIMAGEABLE ACRYLIC POLYMERS, PHOTORESISTS AND PROCESSES FOR MICROLITHOGRAPHY

BACKGROUND OF THE INVENTION

1. Field of the Invention

The present invention pertains to low-polydispersity acrylic polymers useful for photoimaging and photoresist compositions, and to the photoimaging processes which use these compositions. The low-polydispersity polymers of this invention are prepared using controlled radical polymerization (CRP) techniques such as RAFT (reversible addition fragmentation chain transfer) polymerization.

2. Description of Related Art

Polymer products are used as components of imaging and photosensitive systems and particularly in photoimaging systems. In such systems, ultraviolet (UV) light or other electromagnetic radiation impinges on a material containing a photoactive component to induce a physical or chemical change in that material. A useful or latent image is thereby produced which can be processed into a useful image for semiconductor device fabrication.

For imaging features at the submicron level in semiconductor devices, electromagnetic radiation in the far or extreme ultraviolet (UV) is needed. Photolithography at 248 nm exposure is currently in commercial use, and 193 nm exposure is currently being introduced for microelectronics fabrication using design rules for 0.13 µm and below. Photolithography using 157 nm exposure may be needed for 0.07 µm or less design rules.

There is also increasing interest in developing polymerization processes that can be predictably controlled to produce polymers having a specifically desired architecture and molecular weight. One of the means for achieving such results is through a process of "living polymerization." Such a process provides a higher degree of control during the synthesis of polymers having predictably well-defined architecture and molecular weight with narrow dispersity as compared to polymers made by conventional polymerization processes.

RAFT (reversible addition fragmentation chain transfer) polymerization processes have been disclosed for the preparation of low-polydispersity polymers from acrylic, styrenic and selected other vinyl monomers. (WO 98/01478, WO 99/31144 and EP 0 910,587). Fields of application for these RAFT-derived polymers include imaging and electronics (e.g., photoresists).

T.-Y Lee et al., (Advances in Resist Technology and Processing XX, Theodore H. Fedynyshyn, Editor, Proceedings of SPIE, Vol. 5039 (2003), pp 548-557) have disclosed the preparation of acrylate terpolymers using RAFT processes.

There remains a need for photoresists with high transparency at 157-248 nm and good resolution to enable the production of electronic components with smaller and smaller feature sizes.

SUMMARY OF THE INVENTION

This invention provides a low polydispersity acrylic polymer comprising:
 a. a repeat unit derived from an acrylic monomer selected from the group of acrylate esters and methacrylate esters; and
 b. a functional group selected from the group of fluoroalcohol, protected fluoroalcohol and protected acid groups, wherein the protecting group of the protected acid group comprises at least 5 carbon atoms.

In a second aspect, this invention also provides a photoresist comprising:
 a. a photoactive component; and
 b. a low polydispersity polymer comprising at least one repeat unit derived from an acrylic monomer selected from the group of acrylate esters and methacrylate esters.

In a third aspect, this invention provides a process for forming a coated substrate, comprising:
 1. coating a substrate with a mixture comprising:
  a. a low-polydispersity polymer comprising a repeat unit derived from an acrylic monomer selected from the group of acrylate esters and methacrylate esters;
  b. a photoactive component; and
  c. a solvent; and
 2. evaporating the solvent.

In a fourth aspect, this invention provides a process for forming a photoresist image on a substrate, comprising
 a. forming a photoresist layer on a substrate, wherein the photoresist comprises a low-polydispersity polymer of this invention and a photoactive component;
 b. imagewise exposing the photoresist layer to actinic radiation to form imaged and non-imaged areas; and
 c. developing the exposed photoresist layer having imaged and non-imaged areas to form the photoresist image on the substrate.

This invention also provides coated and/or imaged substrates, produced by the coating and imaging processes of this invention.

The present invention also provides a process for producing a low polydispersity polymer, comprising polymerizing a monomer mix comprising a first acrylic monomer containing a functional group selected from the group of fluoroalcohol, protected fluoroalcohol and protected acid groups, wherein the protecting group of the protected acid group comprises at least 5 carbon atoms and one or more other acrylic monomers, in the presence of a source of free radicals and a chain transfer agent to produce an acrylic copolymer, wherein the chain transfer agent has a transfer constant in the range of from 0.1 to 500 and the chain transfer agent has the following structure:

wherein:
R=alkyl, alkenyl, aryl, aralkyl, substituted alkyl, substituted aryl, carbocyclic or heterocyclic ring, alkylthio, alkoxy, or dialkylamino; and
Z=H, alkyl, aryl, aralkyl, substituted alkyl, substituted aryl, carbocyclic or heterocyclic ring, alkylthio, arylthio, alkoxycarbonyl, aryloxycarbonyl, carboxy, acyloxy, carbamoyl, cyano, dialkyl- or diaryl-phosphonato, or dialkyl- or diaryl-phosphinato.

The present invention is also directed to polymers made by the polymerization process of the current invention.

DETAILED DESCRIPTION OF THE INVENTION

In the context of the present invention, low polydispersity polymers are those with polydispersities that are significantly less than those produced by conventional free radical polymerization. In conventional free radical polymerization, polydispersities of the polymers formed are typically in the range of 1.5-2.0 at low monomer conversions (i.e., 0.1% to 10% conversion) and are substantially greater (in the range of 2-10) at higher conversions (i.e., 10-100% conversion). Polymers having polydispersity in the range of 1.05 to 2.0 at conversions of greater than 10% are preferred; polydispersities of 1.05 to 1.3 at high conversion are more preferred.

One of the advantages of the present polymerization system is that by controlling the reaction stoichiometry and the degree of conversion of the monomers into polymer the process produces polymers of predetermined molecular weight and narrow molecular weight distribution over a wide range of monomers and reaction conditions.

Acrylic Monomer

The low-polydispersity polymer comprises a repeat unit derived from an acrylic monomer, $CH_2=CR'CO_2R''$ or $CH_2=C(CH_2OH)CO_2R'''$.

When the acrylic monomer is $CH_2=C(CH_2OH)CO_2R'''$, $R'''$ is a $C_1$-$C_{25}$ alkyl group, optionally substituted by one or more hydroxy, halogen, ether oxygen, ester or ketone carbonyl groups. Preferably $R'''$ contains 1 to 20 carbon atoms. A preferred alkyl group, $R'''$, is one that is acid-labile. Examples of acid-labile alkyl groups include, but are not limited to, tertiary alkyl groups containing 5 or more carbon atoms, such as 2-methyl-2-adamantyl.

When the acrylic monomer is $CH_2=CR'CO_2R''$, $R'$ is H, F, an alkyl group of 1 to 5 carbon atoms, or a fluoroalkyl group of 1 to 5 carbon atoms. $R''$ is a $C_1$-$C_{20}$ acyclic aliphatic group or a cyclic $C_5$-$C_{50}$ or polycyclic $C_7$-$C_{50}$ alkyl group, optionally containing at least one hydroxy functional group, or a functional group of the formula $—C(R^1)(R^2)—[C(R^3)(R^4)]_m—C(R^5)(R^6)—OH$. Preferably $R'$ is an alkyl group of 1 to 5 carbon atoms. Some examples of appropriate monomers are provided below.

When the acrylic monomer is $CH_2=CR'CO_2R''$, a preferred embodiment is when $R''$ is a polycyclic group containing from 5 to 50 carbon atoms, preferably 5 to 30 carbon atoms, optionally with at least one hydroxyl substituent. $R''$ can also be optionally substituted by one or more halogen, ether oxygen, ester or ketone carbonyl groups. Preferred polycyclic acrylic monomers include 3-hydroxy-1-adamantyl methacrylate ($CH_2=CH_3CO_2R''$, wherein $R''$ is 3-hydroxy-1-adamantyl), 2-ethyl-2-adamantyl methacrylate, 2-methyl-2-adamantyl methacrylate, 2,3-NBFOHMA, and 5-methacryloyloxy-2,6-norbornanecarbolactone. $R''$ can be an acid-labile group. Preferred cyclic acrylic monomers include γ-butyrolactone methacrylate, both α- and β-isomers. $R''$ can have one or more fluorine substituents.

Alternatively, $R''$ can be a functional group of the formula:

$$—C(R^1)(R^2)—[C(R^3)(R^4)]_m—C(R^5)(R^6)—OH,$$

wherein m=0, 1, 2, 3, 4 or 5;

$R^1$ and $R^2$ are independently $C_1$-$C_6$ alkyl; $C_1$-$C_6$ alkyl substituted with an ether oxygen; or $R^1$ and $R^2$ taken together form a 3- to 8-membered ring, optionally substituted with an ether oxygen, provided that the carbon attached to $R^1$ and $R^2$ is not at a bridgehead position;

$R^3$ and $R^4$ are independently H; $C_1$-$C_6$ alkyl; $C_1$-$C_6$ alkyl substituted with an ether oxygen; or $R^3$ and $R^4$ taken together form a 3- to 8-membered ring, optionally substituted with an ether oxygen;

$R^5$ and $R^6$ are independently H; $C_1$-$C_6$ alkyl; $C_1$-$C_6$ alkyl substituted with an ether oxygen; or $R^5$ and $R^6$ taken together form a 3- to 8-membered ring, optionally substituted with an ether oxygen; or $R^1$ and $R^5$ taken together with $—[C(R^3)(R^4)]_m—$ form a 4- to 8-membered ring, provided that the carbon attached to $R^1$ and $R^2$ is not at a bridgehead position.

PinMAc (2-methyl-2-propenoic acid, 2-hydroxy-1,1,2-trimethylpropyl ester), and the acrylate analog, PinAc, are preferred acyclic acrylic monomers.

Acrylate and methacrylate monomers suitable for use in this invention include, but are not limited to: 2-methyl-2-adamantyl (meth)acrylate; 2-ethyl-2-adamantyl-(meth)acrylate; 2-propyl-2-adamantyl-(meth)acrylate; 2-(1-adamantyl)-2-propyl-(meth)acrylate; α-(γ-butyrolactone)-(meth)acrylate; β-(γ-butyrolactone)-(meth)acrylate; 3-hydroxy-1-adamantyl-(meth)acrylate; 8-methyltricyclo[5.2.1]decan-8-yl-(meth)acrylate; 8-ethyltricyclo[5.2.1]decan-8-yl-(meth)acrylate; 2-(4-methoxybutyl)-2-adamantyl-(meth)acrylate; mevalonic lactone-(meth)acrylate; PinAc; PinMAc; 4-hydroxy-1-methylcyclohexyl-(meth)acrylate; 1-methylcyclopentyl-(meth)acrylate; 1-ethylcyclopentyl-(meth)acrylate; 3-(2,2-bis(trifluoromethyl)-2-hydroxyethyl)-endo-2-(2-methylpropenoyl)-bicyclo[2.2.1]heptane; 3-(2,2-bis(trifluoromethyl)-2-hydroxyethyl)-endo-2-(propenoyl)-bicyclo [2.2.1]heptane; and 5-(meth)acryloyloxy-2,6-norbornanecarbolactone.

Functional Groups

A polymer of this invention can include a repeat unit derived from acrylic monomer containing a functional group derived from a fluoroalcohol functional group. This functional group contains fluoroalkyl groups, designated $R_f$ and $R_f'$, which can be partially or fully fluorinated alkyl groups. $R_f$ and $R_f'$ are the same or different fluoroalkyl groups of from 1 to 10 carbon atoms or taken together are $(CF_2)_n$ wherein n is 2 to 10. The phrase "taken together" indicates that $R_f$ and $R_f'$ are not separate, discrete fluorinated alkyl groups, but that together they form a ring structure such as is illustrated below in case of a 5-membered ring:

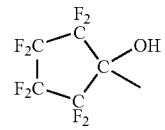

$R_f$ and $R_f'$ must be sufficiently fluorinated to impart acidity to the hydroxyl (—OH) of the corresponding fluoroalcohol functional group, such that the hydroxyl proton can be substantially removed in basic media (e.g., aqueous sodium hydroxide or tetraalkylammonium hydroxide solution). Preferably, there is sufficient fluorine in the fluoroalcohol functional group such that the hydroxyl group has a pKa value of 5-11. Preferably, $R_f$ and $R_f'$ are independently perfluoroalkyl groups of 1 to 5 carbon atoms, most preferably, trifluoromethyl ($CF_3$). The number of fluoroalcohol groups is determined for a given composition by optimizing the amount needed for good development in aqueous alkaline developer.

More specifically, the low polydispersity polymers can comprise a repeat unit derived from an acrylic monomer containing a fluoroalcohol functional group having the structure:

$$—X_r(CH_2)_qC(R_f)(R_f')OH$$

wherein $R_f$ and $R_f'$ are the same or different fluoroalkyl groups of from 1 to 10 carbon atoms, or taken together are $(CF_2)_n$; n is an integer from 2 to 10; X is selected from the group consisting of S, O, N, and P; q=0 and r=0; or q=1 and r=0 or 1. Preferably, r=0. When r=1, preferably, X is O (oxygen).

Protecting Groups for Removal by PAC Catalysis

In addition to, or in place of a fluoroalcohol group, the polymers of the resist compositions of this invention can contain one or more components having protected acidic fluorinated alcohol groups (e.g., —C($R_f$)($R_f'$)$OR_a$, where $R_a$ is not H) or other acid groups that can yield hydrophilic groups by the reaction with acids or bases generated photolytically from photoactive compounds (PACs). A given protected fluorinated alcohol group contains a protecting group that protects the fluorinated alcohol group or other acid group from exhibiting its acidity while in this protected form. A given protected acid group is normally chosen on the basis of its being acid-labile, such that when acid is produced upon imagewise exposure, it will catalyze deprotection of the protected acidic fluorinated alcohol groups and production of hydrophilic acid groups that are necessary for development under aqueous conditions.

An alpha-alkoxyalkyl ether group (i.e., $R_a$=$CH_2OR_b$, $R_b$=$C_1$-$C_{11}$ alkyl) is a preferred protecting group for the fluoroalcohol group in order to maintain a high degree of transparency in the photoresist composition. An illustrative, but non-limiting, example of an alpha-alkoxyalkyl ether group that is effective as a protecting group, is methoxy methyl ether (MOM). A protected fluoroalcohol with this particular protecting group can be obtained by reaction of chloromethylmethyl ether with the fluoroalcohol. An especially preferred protected fluoroalcohol group has the structure:

—C($R_f$)($R_f'$)O—$CH_2OCH_2R_{15}$ wherein, $R_f$ and $R_f'$ are the same or different fluoroalkyl groups of from 1 to 10 carbon atoms or taken together are $(CF_2)_n$ wherein n is 2 to 10; $R_{15}$ is H, a linear alkyl group of 1 to 10 carbon atoms, or a branched alkyl group of 3 to 10 carbon atoms.

Carbonates formed from a fluorinated alcohol and a tertiary aliphatic alcohol can also be used as protected acidic fluorinated alcohol groups.

The polymers of this invention can also contain other types of protected acidic groups that yield an acidic group upon exposure to acid. Examples of such types of protected acidic groups include, but are not limited to: A) alkyl esters, or substituted alkyl esters, capable of forming, or rearranging to, a tertiary cation containing 5 or more carbon atoms; B) esters of lactones; C) acetal esters; D) β-cyclic ketone esters; E) α-cyclic ether esters; and F) esters which are easily hydrolyzable because of anchimeric assistance, such as MEEMA (methoxy ethoxy ethyl methacrylate).

Some specific examples in category A) are 2-methyl-2-adamantyl ester and isobornyl ester.

In this invention, a functional group (e.g., a fluoroalcohol, protected fluoroalcohol or protected acid group) is generally present in at least one monomer that is polymerized to form a given polymeric base resin of this invention. Alternatively, a polymeric base resin can be formed by polymerization of an acid-containing monomer and then subsequently acid functionality in the resulting acid-containing polymer can be partially or wholly converted by appropriate means to derivatives having protected acid groups.

RAFT Polymerization Process

We have discovered a novel free radical polymerization process and novel polymers produced therefrom. The process is directed to polymerizing a monomer mix in the presence of a source of free radicals and at least one of certain sulfur-based chain transfer agents (CTAs), chosen so as to confer living characteristics. By utilizing these CTAs, acrylic polymers of controlled molecular weight and low polydispersity can be obtained.

The sulfur-based CTAs suitable for use in the present invention have a chain transfer constant in the range of from 0.1 to 5000, preferably in the range of from 1 to 2000, and more preferably in the range of from 10 to 500. If the chain transfer constant of the CTA exceeds the upper limit of the range, substantially no polymerization occurs; if it falls below the lower limit, it is not possible to produce polymers having low polydispersity.

"Chain transfer constant" means the ratio of the rate constant for chain transfer to the rate constant for propagation at zero conversion of monomer and CTA. If chain transfer occurs by addition-fragmentation, the rate constant for chain transfer ($k_{tr}$) is defined as follows:

$$k_{tr} = k_{add} \times \frac{k_\beta}{k_{-add} + k_\beta}$$

where $k_{add}$ is the rate constant for addition to the CTA and $k_{-add}$ and $k_\beta$ are the rate constants for fragmentation in the reverse and forward directions respectively.

Suitable chain transfer agents have the following formula:

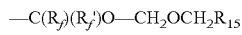

wherein:
R=alkyl, alkenyl, aryl, substituted alkyl, substituted aryl, aralkyl, carbocyclic or heterocyclic ring, alkylthio, or dialkylamino; and
Z=H, alkyl, aryl, aralkyl, substituted alkyl, substituted aryl, carbocyclic or heterocyclic ring, alkylthio, substituted alkylthio, arylthio, substituted arylthio, alkoxycarbonyl, aryloxycarbonyl, carboxy, acyloxy, carbamoyl, cyano, dialkyl- or diaryl-phosphonato, or dialkyl- or diaryl-phosphinato.

The preparation of examples of suitable CTAs is disclosed in U.S. Pat. No. 6,512,081, WO 98/01478, WO 99/31144, EP 0 825,247 and EP 0 910,587, which are hereby incorporated by reference. Suitable CTAs include dithioesters, thiocarbonylthio compounds, benzyl(1,2-benzenedicarboximido)carbodithioate, 2-cyanoprop-2-yl 1-pyrrolecarbodithioate, 2-cyanobut-2-yl 1-pyrrolecarbodithioate, benzyl 1-imidazolecarbodithioate, xanthate derivatives such as O-ethyl S-(1-phenylethyl) xanthate, O-ethyl S-(2-ethoxycarbonylprop-2-yl) xanthate, and O-ethyl S-(2-cyanoisopropyl) xanthate. Preferred CTAs include dithioesters and trithiocarbonates, especially S-cyanomethyl-S-dodecyltrithiocarbonate and 4-cyano-4-(dodecylsulfanylthiocarbonyl)-sulfanyl pentanoic acid. In general, R must be capable of producing a radical that is comparable in stability to the growing polymer radical. Thus for acrylates and styrenics R can be a primary or preferably a secondary alkyl group as long as it is substituted with a CN, $CO_2H$, $CO_2R$ or phenyl group. For methacrylates, CTAs with tertiary leaving groups are preferred. These CTAs contain at least one quaternary carbon-sulfur bond, e.g., CTAs in which R is —C($CH_3$)(CN)$CH_2CH_2CO_2H$.

The source of free radicals suitable for use in the present invention includes those compounds that provide free radicals that add to monomers to produce propagating radicals. Propagating radicals are radical species that have added one or more monomer units and are capable of adding further monomer units.

The amount of the free radical initiator used should be chosen to keep the free radical concentration low. The molar ratio of free radical initiator to the RAFT chain transfer agent should be about 0.05-10, preferably 0.1-2, and most preferably 0.2-1.

It should be noted that the molecular weight of the polymer is determined by the molar ratio of RAFT chain transfer agent to monomer. In principle, each polymer chain will have a RAFT end group, so the number of RAFT molecules will determine the number of polymer chains, and hence the molecular weight.

The source of initiating radicals can be any suitable method of generating free radicals that provides free radicals that add to monomers to produce propagating radicals. This includes such sources as the thermally induced homolytic scission of a suitable compound(s) (such as peroxides, peroxyesters, hydroperoxides, persulfates, perborates, or azo compounds), the spontaneous generation from monomer, redox initiating systems, photochemical initiating systems or high energy radiation such as electron beam, X- or γ-radiation. The initiating system is chosen such that under the reaction conditions there is no substantial adverse interaction of the initiator or the initiating radicals with the transfer agent under the conditions of the reaction. The initiator should also have the requisite solubility in the reaction medium or monomer mixture.

Examples of suitable sources of free radicals for the process include azo compounds and peroxides such as: 2,2'-azobis-(isobutyronitrile), 2,2'-azobis(2-cyano-2-butane), dimethyl 2,2'-azobis(methyl isobutyrate), 4,4'-azobis(4-cyanopentanoic acid), 4,4'-azobis(4-cyanopentan-1-ol), 1,1'-azobis(cyclohexanecarbonitrile), 2-(t-butylazo)-2-cyanopropane, 2,2'-azobis[2-methyl-N-(1,1)-bis-(hydoxymethyl)-2-hydroxyethyl]propionamide, 2,2'-azobis[2-methyl-N-hydroxyethyl)]-propionamide, 2,2'-azobis(N,N'-dimethylene-isobutyramidine) dihydrochloride, 2,2'-azobis(2-amidinopropane) dihydrochloride, 2,2'-azobis(N,N'-dimethyleneisobutyramine), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl]propionamide), 2,2'-azobis[2-methyl-N-(2-hydroxyethyl) propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butyl peroxyneodecanoate, t-butyl-peroxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxy-disulfate, ammonium peroxydisulfate, di-t-butyl hyponitrite, di-t-butyl-peroxide or dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems.

Redox initiator systems are chosen to have the requisite solubility in the reaction medium or monomer mixture and have an appropriate rate of radical production under the conditions of the polymerization. These initiating systems may include combinations of oxidants (potassium peroxydisulfate, hydrogen peroxide, t-butyl hydroperoxide) and reductants (iron (II), titanium (III), potassium thiosulfite, potassium bisulfite). Other suitable initiating systems are described in recent texts. See, for example, Moad and Solomon "The Chemistry of Free Radical Polymerization", Pergamon, London, 1995, pp 53-95.

The monomers or comonomers of the monomer mix include one or more acrylate and/or methacrylate esters.

It should be understood that it is also possible, if desired, to produce polymers with broad, yet controlled, polydispersity or multimodal molecular weight distribution by controlled addition of the CTA over the course of the polymerization process of the present invention.

The invention can be used to narrow the polydispersity of polymers formed in polymerizations that would otherwise produce polymers of broad or very broad polydispersities. In this circumstance a preferred polydispersity is one which is less than that formed in the absence of the CTA.

The molecular weight and the polydispersity of the polymer made by the process of the present invention are controlled by one or more of the following:

The polymerization conditions are selected to minimize the number of chains formed from initiator-derived radicals to an extent consistent with obtaining an acceptable rate of polymerization. Termination of polymerization by radical-radical reaction will lead to chains that contain no active group and therefore cannot be reactivated. The rate of radical-radical termination is proportional to the square of the radical concentration. Furthermore, in the synthesis of block, star or branched polymers, chains formed from initiator-derived radicals will constitute an architecturally different polymer impurity in the final product. These reaction conditions therefore require careful choice of the initiator concentration and, where appropriate, the rate of the initiator feed.

It is also desirable to choose other components of the polymerization medium (for example, the solvents, surfactants, additives, and initiator) such that they have a low transfer constant towards the propagating radical. Chain transfer to these species will lead to the formation of chains that do not contain the active group.

As a general guide in choosing conditions for the polymerization of narrow polydispersity polymers, the concentration of initiator(s) and other reaction conditions [solvent(s) if any, reaction temperature, reaction pressure, surfactants if any, other additives]should be chosen such that the molecular weight of polymer formed in the absence of the CTA is at least twice that formed in its presence. In polymerizations where radical-radical termination is solely by disproportionation, this equates to choosing an initiator concentration such that the total moles of initiating radicals formed during the polymerization is in the range of $10^{-6}$ times to 1.0 times that of the total moles of CTA.

Thus, by varying the ratio of the total number of moles of the CTA to the total number of moles of the free radical initiator added to a polymerization medium, the polydispersity of the resulting polymer is controlled. Thus, by decreasing the foregoing ratio, a polymer of lower polydispersity is obtained and by increasing the ratio, a polymer of higher polydispersity is obtained.

With these provisos, the polymerization process according to the present invention is performed under the conditions typical of conventional free-radical polymerization. Polymerization employing the CTAs of the present invention is suitably carried out with temperatures during the reaction in the range 30° C. to 120° C., preferably in the range 60° C. to 100° C.

The process of this invention can be carried out in emulsion, solution or suspension in either a batch, semi-batch, continuous, or feed mode. The use of CTA's in an otherwise-conventional polymerization procedure can be used to produce narrow polydispersity polymers by the process of this invention. For lowest polydispersity polymers, the CTA is added before polymerization is commenced. For example, when carried out in batch mode in solution, the reactor is typically charged with CTA and monomer or medium plus monomer. To the mixture is then added the desired amount of initiator and the mixture is heated for a time that is dictated by the desired conversion and molecular weight.

In the case of emulsion or suspension polymerization the polymerization medium will often be predominantly water and the conventional stabilizers, dispersants and other additives can be present.

For solution polymerization, the polymerization medium can be chosen from a wide range of media to suit the monomer(s) being used. Suitable polymerization media include: aromatic hydrocarbons, such as, petroleum naphtha or xylenes; fluorocarbons, such as 1,1,1,3,3-pentafluorobutane; ketones, such as methyl amyl ketone, methyl isobutyl ketone, methyl ethyl ketone and acetone; esters, such as ethyl acetate, butyl acetate and hexyl acetate; and glycol ether esters, such as propylene glycol monomethyl ether acetate.

As has already been stated, the use of feed polymerization conditions allows the use of CTAs with lower transfer constants and allows the synthesis of polymers that are not readily achieved using batch polymerization processes. If the polymerization is carried out as a feed system the reaction can be carried out as follows. The reactor is charged with the chosen polymerization medium, the CTA and optionally a portion of the monomer mixture. Into a separate vessel is placed the remaining monomer mixture. The free radical initiator is dissolved or suspended in polymerization medium in another separate vessel. The medium in the reactor is heated and stirred while the monomer mixture+medium and initiator+medium are introduced, for example by a syringe pump or other pumping device. The rate and duration of feed is determined largely by the quantity of solution, the desired monomer/CTA/initiator ratio and the rate of the polymerization. When the feed is complete, heating may be continued for an additional period. Sequential addition of different monomers can give a block or gradient copolymer.

Preferred CTAs are dithioesters and trithiocarbonates, such as S-cyanomethyl-S-dodecyltrithiocarbonate and 4-cyano-4-(dodecylsulfanylthiocarbonyl)sulfanyl pentanoic acid. The polymerization pressure can range from 0 to about 10,000 psig, preferably from about 0 psig to about 1,000 psig.

An advantage of the process of the present invention is that by successively adding different monomers to the reaction mixture, block polymers of low polydispersity and desired molecular weight can be produced.

Following completion of the polymerization, the polymer can be isolated by stripping off the medium and unreacted monomer(s) or by precipitation with a non-solvent. Alternatively, the polymer solution/emulsion can be used as such, if appropriate to its application.

The process of the present invention can be used under various reaction conditions to produce polymers having low polydispersity. By varying the rate of monomer addition or by varying the sequence in which the monomers are added to the polymerization medium, the process of the present invention may be used to produce structurally diverse polymers ranging from random but compositionally homogeneous polymers to block and multi-block and gradient polymers. By selecting the functionalities desired, an end-functional polymer of specific end functionalities can be readily produced.

Photoactive Component (PAC)

The polymers of this invention can be used to make photoresists by combining the polymers with at least one photoactive component, a compound that affords either acid or base upon exposure to actinic radiation. If an acid is produced upon exposure to actinic radiation, the PAC is termed a photoacid generator (PAG). If a base is produced upon exposure to actinic radiation, the PAC is termed a photobase generator (PBG). Several suitable photoacid generators are disclosed in WO 00/66575.

Suitable photoacid generators for this invention include, but are not limited to, 1) sulfonium salts (structure I), 2) iodonium salts (structure II), and 3) hydroxamic acid esters, such as structure III.

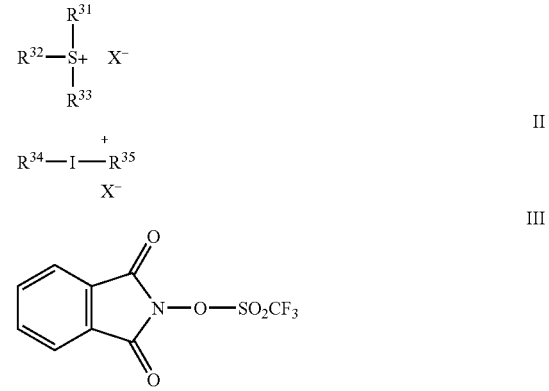

In structures I-II, $R^{31}$-$R^{35}$ are independently substituted or unsubstituted aryl or substituted or unsubstituted $C_7$-$C_{20}$ alkylaryl or aralkyl. Representative aryl groups include, but are not limited to, phenyl and naphthyl. Suitable substituents include, but are not limited to, hydroxyl (—OH) and $C_1$-$C_{20}$ alkyloxy (e.g., —$OC_{10}H_{21}$). The anion, $X^-$, in structures I-II can be, but is not limited to, $SbF_6^-$ (hexafluoroantimonate), $CF_3SO_3^-$ -(trifluoromethylsulfonate=triflate), and $C_4F_9SO_3^-$ (perfluorobutylsulfonate).

Dissolution Inhibitors and Additives

Various dissolution inhibitors can be added to photoresists derived from the polymers of this invention. Ideally, dissolution inhibitors (DIs) for far and extreme UV resists (e.g., 193 nm resists) should be designed/chosen to satisfy multiple materials needs including dissolution inhibition, plasma etch resistance, and adhesion behavior of resist compositions comprising a given DI additive. Some dissolution inhibiting compounds also serve as plasticizers in resist compositions. Several suitable dissolution inhibitors are disclosed in WO 00/66575.

Positive-Working and Negative-Working Photoresists

The photoresists of this invention can either be positive-working photoresists or negative-working photoresists, depending upon choice of components in the polymer, the presence or absence of optional dissolution inhibitor and crosslinking agents, and the choice of developer (solvent used in development). In positive-working photoresists, the resist polymer becomes more soluble and/or dispersible in a solvent used in development in the imaged or irradiated areas whereas in a negative-working photoresist, the resist polymer becomes less soluble and/or dispersible in the imaged or irradiated areas. In one preferred embodiment of this invention, irradiation causes the generation of acid or base by the photoactive component discussed above. The acid or base can catalyze removal of protecting groups from the protected fluoroalcohol and optionally other protected acidic groups present in the polymer.

Development in an aqueous base such a tetramethylammonium hydroxide would result in the formation of a positive image whereas development in an organic solvent or critical fluid (having moderate to low polarity), would result in a negative-working system in which exposed areas remain and unexposed areas are removed. Positive-working photoresists are preferred. A variety of different crosslinking agents can be employed as required or optional photoactive component(s) in the negative-working mode of this invention. (A crosslinking agent is required in embodiments that involve insolubilization in developer solution as a result of crosslinking, but is optional in preferred embodiments that involve insolubilization in developer solution as a result of polar groups being formed in exposed areas that are insoluble in organic solvents and critical fluids having moderate/low polarity). Suitable crosslinking agents include, but are not limited to, various bis-azides, such as 4,4'-diazidodiphenyl sulfide and 3,3'-diazidodiphenyl sulfone. Preferably, a negative-working resist composition containing a crosslinking agent(s) also contains suitable functionality (e.g., unsaturated C=C bonds) that can react with the reactive species (e.g., nitrenes) that are generated upon exposure to UV to produce crosslinked polymers that are not soluble, dispersed, or substantially swollen in developer solution, that consequently imparts negative-working characteristics to the composition.

Other Components

Photoresists of this invention can contain additional optional components. Examples of optional components include, but are not limited to, resolution enhancers, adhesion promoters, residue reducers, coating aids, plasticizers, and $T_g$ (glass transition temperature) modifiers.

Imaging Process

Imagewise Exposure

The photoresist compositions of this invention are sensitive in the ultraviolet region of the electromagnetic spectrum and especially to those wavelengths ≦365 nm. Imagewise exposure of the resist compositions of this invention can be done at many different UV wavelengths including, but not limited to, 365 nm, 248 nm, 193 nm, 157 nm, and lower wavelengths. Imagewise exposure is preferably done with ultraviolet light of 248 nm, 193 nm, 157 nm, or lower wavelengths, and most preferably it is done with ultraviolet light of 193 nm, 157 nm, or lower wavelengths. Imagewise exposure can either be done digitally with a laser or equivalent device or non-digitally with use of a photomask. Laser light can also be used with a photomask. Digital imaging with a laser is preferred. Suitable laser devices for digital imaging of the compositions of this invention include, but are not limited to, an argon-fluorine excimer laser with UV output at 193 nm, a krypton-fluorine excimer laser with UV output at 248 nm, and a fluorine (F2) laser with output at 157 nm. Since use of UV light of lower wavelength for imagewise exposure corresponds to higher resolution (lower resolution limit), the use of a lower wavelength (e.g., 193 nm or 157 m or lower) is generally preferred over use of a higher wavelength (e.g., 248 nm or higher).

Development

The polymers in the resist compositions of this invention must contain sufficient functionality for development following imagewise exposure to UV light. Preferably, the functionality is acid or protected acid such that aqueous development is possible using a basic developer such as sodium hydroxide solution, potassium hydroxide solution, alkylammonium hydroxide or ammonium hydroxide solution.

When an aqueous processable photoresist is coated or otherwise applied to a substrate and imagewise exposed to UV light, development of the photoresist composition may require that the binder material contain sufficient acid groups (e.g., fluoroalcohol groups) and/or protected acid groups that are at least partially deprotected upon exposure to render the photoresist (or other photoimageable coating composition) processable in aqueous alkaline developer. In case of a positive-working photoresist, the photoresist layer will be removed during development in portions which have been exposed to UV radiation but will be substantially unaffected in unexposed portions. Development of positive-working resists typically consists of treatment by aqueous alkaline systems, such as aqueous solutions containing 0.262 N tetramethylammonium hydroxide, at 25° C. for 2 minutes or less. In case of a negative-working photoresist, the photoresist layer will be removed during development in portions which are unexposed to UV radiation, but will be substantially unaffected in exposed portions. Development of a negative-working resist typically consists of treatment with a critical fluid or an organic solvent.

A critical fluid, as used herein, is a substance heated to a temperature near or above its critical temperature and compressed to a pressure near or above its critical pressure. Critical fluids in this invention are at a temperature that is higher than 15° C. below the critical temperature of the fluid and are at a pressure higher than 5 atmospheres below the critical pressure of the fluid. Carbon dioxide can be used for the critical fluid in the present invention. Various organic solvents can also be used as developer in this invention. These include, but are not limited to, halogenated solvents and non-halogenated solvents. Halogenated solvents are preferred and fluorinated solvents are more preferred. A critical fluid can comprise one or more chemical compounds.

Substrate

The substrate employed in this invention can illustratively be silicon, silicon oxide, silicon oxynitride, silicon nitride, or various other materials used in semiconductive manufacture.

EXAMPLES

|             | Chemicals/Monomers |
|-------------|--------------------|
| 2,3-NBFOHMA | 3-(2,2-bis(trifluoromethyl)-2-hydroxyethyl)-endo-2-(2-methylpropenoyl)-bicyclo[2.2.1]heptane |
| HADMA       | Hydroxy adamantyl methacrylate Idemitsu Chemical USA Southfield, MI |
| PGMEA       | Propylene glycol methyl ether acetate Aldrich Chemical Co., Milwaukee, WI |
| PinMAc      | 2-Propenoic acid, 2-hydroxy-1,1,2-trimethylpropyl ester [CAS Reg number 97325-36-5] |
| THF         | Tetrahydrofuran Aldrich Chemical Co., Milwaukee, WI |
| Vazo ® 88   | 1,1'-Azobis(cyclohexanecarbonitrile) [CAS Registry number 2094-98-6] E. I. du Pont de Nemours and Company, Wilmington, DE |
| V601        | 2,2'-azobis(methyl isobutyrate) Waco Chemicals USA Richmond, VA |

Example 1

Preparation of exo-2-(2,2-bis(trifluoromethyl)-2-hydroxyethyl)-endo-3-hydroxy-bicyclo[2.2.1]heptane and exo-2-(2,2-bis(trifluoromethyl)-2-hydroxyethyl)-exo-3-hydroxy-bicyclo[2.2.1]heptane. Sequential Addition method, giving diastereomeric mixture of diols A 3-neck flask, fitted with a thermowell, overhead stirrer, septum and $N_2$ inlet, was charged with norcamphor (22.0 g, 200 mmol) and t-butyl methyl ether (50 mL). The solution was cooled to −15° C., treated with hexafluorobutene epoxide (41 g, 228 mmol) by canula, and then dropwise with a solution of lithium bis(trimethylsilyl)amide (36.8 g, 220 mmol) in 2/1 t-butyl methyl ether/heptane at a rate to control the temperature at −15° C. The mixture was stirred at −15° C. for 15 min, then allowed to warm to 0° C. and stirred for 40 min. The mixture was further warmed to room temperature, then to 28.5° C. as an exotherm took place. The mixture was stirred for an additional 1.75 hr after the reaction returned to room temperature. The lithium salt of the resulting hemiketal was reduced directly by treatment with lithium borohydride as follows.

The above reaction mixture was cooled to ca. 0° C. and treated dropwise with a solution of lithium borohydride (1.45 g, 66.7 mmol) in THF (10 mL). The mixture was stirred for 30 hr at 0° C. and was then allowed to warm slowly to room temperature and was stirred at ambient temperature for 16 hr. The mixture was cooled to 0° C., treated dropwise with water (5 mL) and then dropwise with 100 mL of 2N HCl. The mixture was warmed to room temperature, and the pH was adjusted to ca. 5 by addition of more HCl. The organic layer was separated, dried ($Na_2SO_4$, MgSO4), and stripped to give 69 g of crude oil.

Kugelrohr distillation gave 49.1 g of product collected between 80° C. and 105° C. (0.05 mm). $^{19}F$ NMR analysis showed an isomeric mixture of diols (isomer ratio=75/25) and ca. 95% purity; $^1H$ NMR analysis featured signals at 3.8 (m, a=0.7), 3.28 to 3.2 (m, a=5.3). Distilled material was crystallized from hot hexane (ca. 75 mL) using progressive cooling to −10° C. with occasional agitation to give a first crop, 41.5 g. $^{19}F$ NMR ($C_6D_6$): two sets of quartets, −74.83 and −79.10 (J=9.8; a=32.3), and −76.79 and −78.73 (J=9.8; a=100). $^1H$ NMR: 7.02 (s, a=0.24), 5.35 (s, a=0.76), 3.22 (m) and 3.17 (d, J=6.6 Hz, combined a=1.00; ratio of these two signals is 75/25), 2.1 to 0.52 (series of m's, combined a=12.6); signals at 3.22 and 3.17 are assigned to C$\underline{H}$OH, down-field singlets are assigned to the fluoroalcohol OH groups.

Example 2

Preparation of exo-3-(2,2-bis(trifluoromethyl)-2-hydroxyethyl)-endo-2-(2-methylpropenoyl)-bicyclo[2.2.1]heptane and exo-3-(2,2-bis(trifluoromethyl)-2-hydroxyethyl)-exo-2-(2-methylpropenoyl)-bicyclo[2.2.1]heptane A solution of exo-2-(2,2-bis(trifluoromethyl)-2-hydroxyethyl)-3-hydroxy-bicyclo[2.2.1]heptane (11.68 g, 40.0 mmol) in t-butyl methyl ether (40 mL) was cooled to −15° C. and treated drop-wise with a solution of potassium t-butoxide (9.42 g, 80 mmol) in tetrahydrofuran (50 mL) while maintaining the temperature below −10° C. The mixture was stirred for 10 min at −15° C. and then treated dropwise with methacrylic anhydride (6.78 g, 44 mmol) by syringe. The mixture was stirred for 1 hr at −15° C., then warmed to 0° C. for 3 hr. The reaction was quenched by dropwise addition of 20 mL 2 N HCl. The pH of the bottom layer was adjusted to ca. 6-7, and the layers were separated. The organic layer was diluted with t-butyl methyl ether, washed twice with sodium bicarbonate to remove methacrylic acid, then with distilled water. The organic layer was dried and methoxyphenyl (30 mg) and phenothiazine (50 mg) were added. Solvent was stripped to give 15 g of crude product which was passed through a column of neutral alumina (4"×¾") using 80/20 hexane/t-butyl methyl ether. Evaporation of the first 250 mL eluent provided 11.1 g of colorless liquid. Phenothiazine (50 mg) was added as stabilizer. Kugelrohr distillation provided 9.54 g, bp 73°-78° C./0.03 mm. GC showed two components, 8.18 and 8.26 min, area ratio=30/70, in good agreement with $^{19}F$ NMR analysis ($C_6D_6$): 2 isomers, major with equal intensity quartets at −75.26 and −78.80 (70%), minor with quartets at −76.86 and −78.66 (30%). Purity>98%.

$^1H$ NMR ($C_6D_6$) showed a spectrum consistent with 2 isomers (30/70), with minor vinyl signals at 5.98 and 5.15 (m), major vinyl signals at 5.93 and 5.08 (m), major OH at 5.25, minor OH at 4.80, minor C$\underline{H}$O at 4.45 (d of unresolved m's, J=7.3), major C$\underline{H}$O at 3.85 (pseudo-triplet), other multiplets ca. 2.25 to 0.70.

Example 3

In-Situ Alkylation of Bicyclo[2.2.1]heptan-2-one Enolate with Hexafluorobutene Epoxide: Formation of Cyclic Hemiketal A 3-neck flask fitted with a thermowell, overhead stirrer, septum, and nitrogen atmosphere inlet was charged with norcamphor (14.9 g, 135 mmol) and t-butyl methyl ether (35 mL). The solution was cooled to −15° C. and HFIBO (28 g, 154 mmol) was added by canula. The resulting solution was treated dropwise with a solution of lithium bis(trimethylsilyl) amide (24.8 g, 148.5 mmol) in 2/1 t-butyl methyl ether/heptane at a rate to control temperature at −15° C. The mixture was stirred at −15° C. for 15 min, then allowed to warm to 0° C. and stirred for 40 min. The mixture was warmed to room temperature and stirred for 2 hr. The reaction mixture was cooled and quenched by addition of water (5 mL) followed by 75 mL of 2N HCl. Additional HCl was added to lower the pH to ca. 3.5. Layers were separated, and the organic phase was dried ($Na_2SO_4$, $MgSO_4$), filtered, and stripped. A small volume of hexane was added and evaporated under vacuum to give 34.31 g (87.5%) of white solid. $^{19}F$ NMR showed an $A_3B_3$ pattern at −75.62, −75.82 (ca. 90%) and another $A_3X_3$ set at −76.6, −79.0 (ca. 10%). The minor set of signals is believed due to the ring-opened, or ketone form. Recrystallization from hexane (60 mL; seeded, then cooled) gave 27.3 g (70%) of white solid, mp=75-82° C. Single crystal X-ray structure analysis demonstrated that the new carbon-carbon bond was formed on the exo face of the bicyclic framework.

Example 4

Preparation of exo-2-(2,2-bis(trifluoromethyl)-2-hydroxyethyl)-endo-3-hydroxy-bicyclo[2.2.1]heptane Sodium bis(2-methoxyethoxy)aluminum Hydride Reduction of Norcamphor/HFIBO Adduct—Protonated Form The cyclic hemiketal prepared from bicyclo[2.2.1]heptan-2-one and hexafluorobutene epoxide as described above in Example 3 was used for this example. A solution of the cyclic hemiketal (21.8 g, 75.3 mmol) in t-butyl methyl ether (150 mL) was cooled to 0° C. and treated dropwise with a solution of sodium bis(2-methoxyethoxy)aluminum hydride in toluene (24.6 g of 65% solution) over a 40 min period. Gas evolution took place readily. The resulting mixture was stirred for 0.5 hr at 0° C., then warmed to room temperature and stirred for 2 hr. The cooled reaction mixture was quenched by addition of water (7.5 mL) and 120 mL of 3N HCl. Layers were separated and the aqueous phase was extracted once with t-butyl methyl ether (80 mL). Combined organic layers were washed with saturated sodium chloride, dried and stripped to give 23.4 g of solid. Kugelrohr distillation gave 21.56 g (98%) of white solid, (bp 74-89° C./0.06 mm).

$^{19}$F NMR ($C_6D_6$) showed product quartets at −76.78 and −78.72; a small amount of starting material (−75.6 and −75.8) was also present. Stereoselectivity was estimated as 99%.

Example 5

Copolymer of 2,3-NBFOHMA/PinMAC

A 3-neck flask fitted with reflux condenser and nitrogen gas inlet with adaptor to vacuum for de-gassing the reaction mixture before initiation, thermowell, and stir-bar was charged with the branched trithiocarbonate RAFT agent, $C_{12}H_{25}SC(S)SC(CH_3)(CN)CH_2CH_2CO_2H$ (FW=403.66; 464 mg, =1.15 mmol), propylene glycol methyl ether acetate (20 mL), the diastereomeric monomer mixture produced as described in Example 2 (above), PinMac (FW=186; wt=1.64 g, 8.82 mmol), and Vazo®88 (38 mg, 0.15 mmol). The reaction mixture was cooled in ice and several vacuum/nitrogen fill cycles were applied to the system. The temperature was increased to 90° C. over a 0.5 hr time interval. Temperature was maintained at 90° C. for 23 hr.

The reaction solution was cooled to room temperature and added to hexane (350 mL) drop-wise with rapid stirring. The precipitated polymer was collected by filtration. The product was air-dried, then dried in the vacuum oven (60° C., $N_2$ purge, 18 hr) to provide 9.91 g (88.6%). $^1$H NMR (THF-d8): 6.9 to 6.1 (bd singlets, with maxima at 6.7 and 6.4; combined a=1.00; ca. 30/70 ratio), 4.7 to 4.15 (bd m, a=1.02), 2.7 to 0.85 (bd m's, integral obscured by solvent peaks; geminal $CH_3$ group signals at 1.55 and 1.25. $^{19}$F NMR (THF-d8): equal intensity bd singlets at −78.40 and −80.21.

Size exclusion chromatography (THF, RI detector, polystyrene standards) analysis of the final product gave $M_n$=6520, $M_w$=7690 and $M_w/M_n$=1.18.

TGA ($N_2$, after: sample re-dried at 80°): 10% loss at 201° C.

Example 6

The following solution was prepared and magnetically stirred overnight.

| Component | Wt. (g) |
| --- | --- |
| 2,3-NBFOHMA/PinMAc polymer in Example 5 | 2.352 |
| 2-Heptanone | 16.064 |
| Solution of tetrabutylammonium lactate in 2-heptanone prepared as follows: 2.5 g of aqueous tetrabutylammonium hydroxide (40%, Aldrich) was dissolved in | 0.88 |

-continued

| Component | Wt. (g) |
| --- | --- |
| 97.5 g ethyl lactate (Aldrich). 8.5 g of this solution was later dissolved in 8.5 g of 2-heptanone. | |
| 6.82 wt % solution of triphenylsulfonium nonaflate dissolved in 2-heptanone which had been filtered through a 0.45 μm PTFE syringe filter. | 0.704 |

A silicon wafer was prepared by applying an HMDS (hexamethyldisilazane) prime layer using a YES-3 vapor prime oven. A 100% HMDS adhesion promoter from Arch Chemical Co. was used. The oven was programmed to give a prime at 150-300° C. for 160 sec.

The sample was spin-coated using a Brewer Science Inc. Model-100CB combination spin coater/hotplate on a 4 in. diameter Type "P", <100> orientation, silicon wafer. To prepare the coating, 2 ml of the above solution, after filtering through a 0.45 μm PTFE syringe filter, was deposited and spun at 2500 rpm for 60 sec and then baked at 150° C. for 60 sec.

248 nm imaging was accomplished by exposing the coated wafer to light obtained by passing broadband UV light from an ORIEL Model-82421 Solar Simulator (1000 watt) through a 248 nm interference filter which passes about 30% of the energy at 248 nm. Exposure time was 30 seconds, providing an unattenuated dose of 45 mJ/cm². By using a mask with 18 positions of varying neutral optical density, a wide variety of exposure doses were generated. After exposure the exposed wafer was baked at 150° C. for 60 seconds.

Development was performed on a Litho Tech Japan Co. Resist Development Analyzer (Model-790). The wafer was developed for 60 sec in aqueous tetramethylammonium hydroxide (TMAH) solution (Shipley LDD-026W, 2.38% TMAH solution).

This test generated a positive image with a clearing dose of ≈9.7 mJ/cm².

Example 7

Preparation of Norcamphor/HFIBO Adduct

A 3-neck flask fitted with a thermowell, overhead stirrer, septum and $N_2$ inlet was charged with norcamphor (74.5 g, 0.675 mol), t-butyl methyl ether (175 mL), hexafluoro-2-butene epoxide (140 g, 0.77 mol) by canula, and cooled to −15° C. This mixture was treated dropwise with a solution of lithium bis(trimethylsilyl)amide (124 g, 0.743 mol) in t-butyl methyl ether (350 mL) at a rate to control temperature at −15° C. The mixture was stirred at −15° C. for 30 min, 0° C. for 40 min, and room temperature for an additional 1 hr. The reaction mixture was cooled to 0° C., quenched by addition of water (5 mL) and 4N HCl (200 mL). Additional HCl was added to lower the pH of the aqueous layer to ca. 3.5. The layers were separated, and the organic phase was washed with brine solution, dried ($Na_2SO_4$, $MgSO_4$), filtered, and stripped to provide 176.5 g (90%) of white solid.

$^{19}$F showed $A_3B_3$ at −75.62, −75.82 (ca. 90%) and another $A_3X_3$ set at −76.6, −79.0 (ca. 10%). The minor set of signals is believed due to the ring-opened, or ketone form.

Recrystallization from hot hexane (300 mL; seeded, 0° C.) gave 152.1 g (78%) of white solid. The filtrate was further processed to give a second crop, 11.9 g of slightly lower purity.

Example 8

Preparation of exo-2-(2,2-bis(trifluoromethyl)-2-hydroxyethyl)-endo-3-hydroxy-bicyclo[2.2.1]heptane A solution of norcamphor/HFIBO adduct (146.3 g, 0.505 mol) in t-butyl methyl ether (1000 mL) was cooled to −5° C. and treated dropwise with a solution of sodium bis(2-methoxyethoxy)aluminum hydride (112.2 g, 0.56 mol) in toluene, controlling the temperature at −5 to 0° C. The mixture was stirred for 2 hr at 0° C., then warmed to room temperature and stirred for 2 hr. The mixture was cooled and quenched by slow addition of water (25 mL; $H_2$ evolved) and 700 mL of 3N HCl. The layers were separated, and the aqueous phase was extracted once with t-butyl methyl ether (500 mL). The combined organic layers were washed with saturated sodium chloride solution, dried and stripped to give a white solid, 145.3 g (yield estimated as 95%).

Hexane (ca. 300 mL) was added and the product was dissolved at elevated temperature. Crystallization (room temperature) provided crop 1, 129.3 g., mp=77-80° C. $^{19}F$ NMR ($C_6D_6$) showed high isomeric purity, estimated as 99.8%, based on residual signals at ca. −75 and −79.

Example 9

Preparation of exo-3-(2,2-bis(trifluoromethyl)-2-hydroxyethyl)-endo-2-(2-methylpropenoyl)-bicyclo[2.2.1]heptane by Ester Exchange A solution of exo-2-(2,2-bis(trifluoromethyl)-2-hydroxyethyl)-endo-3-hydroxy-bicyclo[2.2.1]heptane (14.6 g, 50 mmol) and methyl methacrylate (50 mL, 0.50 mol) was treated with phenothiazine (15 mg) and titanium 2-ethylhexoxide (0.85 g, 1.5 mmol). The reaction vessel was fitted with a distillation head so that the methanol/methyl methacrylate azeotrope could be removed. The mixture was heated in an oil bath at 100° C.-110° C. After a 5 hr period and removal of a lower-boiling fraction (7 g), $^{19}F$ NMR analysis showed >95% conversion of starting diol and production of a single major product comprising ca. 95% of the signal intensity.

Hexane was added to precipitate a small amount of polymer. The liquid phase was collected after filtration, and the solid was washed with additional hexane. The combined filtrate was evaporated to give 17.41 g of residue that crystallized. The solid was washed twice with cold (−20° C.) hexane and then recrystallized from hexane to provide crystals with unusually good facets, 10.48 g (crop 1), mp 46-47° C. A second crop was obtained by cooling the decanted liquid from crop 1 to lower temperature (ca. −50° C.), 2.50 g with purity estimated as 95%. $^{19}F$ NMR analysis (crop 1, $C_6D_6$): equal intensity quartets at −75.39 and −78.92 (purity>99.5%). $^1H$ NMR (crop 1, $C_6D_6$): 5.93 (unresolved m, a=0.99, vinyl), 5.23 (s, a=0.99, OH), 5.07 (d of quartets, a=1.00, vinyl), 3.84 (m, a=1.00), 2.22 (downfield portion of AB pattern, $J_{AB}$=15.6 Hz, a=1.00), 2.01 (m, a=0.99), 1.92 (dd, J=15.6, 6.08, a=1.00), 1.85 (m, a=1.00), 1.72 to 1.63 (m) and 1.58 (s, a=5.04), 1.36 to 1.25 (m, a=1.01), 1.17 to 1.02 (m, a=2.01), 0.86 and 0.82 (AB pattern with additional coupling, a=2.08).

Example 10

Terpolymer of 2,3-NBFOHMA/MAMA/PinMac

A 3-neck flask fitted with reflux condenser and nitrogen gas inlet with adaptor to vacuum for de-gassing the reaction mixture before initiation, thermowell, and stir-bar was charged with trithiocarbonate RAFT agent $C_{12}H_{25}SC(S)SC(CH_3)(CN)CH_2CH_2CO_2CH_3$ (0.259 g, 0.619 mmol); monomer charge, consisting of 2,3-NBFOHMA (2.10 g, 5.83 mmol), methyladamantyl methacrylate (MAMA, 2.47 g, 10.5 mmol), and PinMac (0.10 g, 0.54 mmol); methyl ethyl ketone (10 mL); and Vazo®88 (45 mg, 0.19 mmol). The reactor was filled with nitrogen, and two more evacuation/fill cycles were performed. The temperature was increased linearly to 83.4° C. over a 1.0 hr time interval. Monomer feed solution was then started, using 2,3-NBFOHMA (8.38 g, 23.3 mmol) and PinMac (0.38 g, 2.04 mmol) in methyl ethyl ketone (15 mL) over a 3 hr interval. The reaction was maintained at 83.4-81.6° C. for 19 hr.

The cooled reaction mixture was added to heptane (400 mL) to provide 10.70 g of solid polymer. A second precipitation using THF/heptane gave 9.58 g after oven drying. SEC analysis showed $M_w$=14,600, $M_n$=11,900, $M_w/M_n$=1.23. $^{13}C$ NMR showed: 2,3-NBFOHMA/MAMA/PinMac=75.4/18.4/6.2. MDSC showed $T_g$ at 161.5° C.

Example 11

Terpolymer of 2,3-NBFOHMA/MAMA/HADMA

A 3-neck flask fitted with reflux condenser and nitrogen gas inlet with adaptor to vacuum for de-gassing the reaction mixture before initiation, thermowell, and stir-bar was charged with trithiocarbonate RAFT agent $C_{12}H_{25}SC(S)SC(CH_3)(CN)CH_2CH_2CO_2CH_3$ (0.920 g, 2.20 mmol), monomer charge, consisting of 2,3-NBFOHMA (2.16 g, 6.0 mmol), MAMA (8.25 g, 35.2 mmol), HADMA (1.42 g, 6.0 mmol), methyl ethyl ketone (10 mL), and V601 (164 mg, 0.7 mmol). The reactor was flushed with nitrogen, and two more evacuation/fill cycles were performed. The temperature was increased to 67° C. over a 1.0 hr time interval. Monomer solution, consisting of 2,3-NBFOHMA (8.64 g), MAMA (2.06 g), HADMA (5.67 g) and methyl ethyl ketone (22 mL) was fed over a 3 hr time interval. The reaction was maintained at 67° C. for 22.3 hr. Aliquot samples were withdrawn at intervals in order to determine residual monomer content and polymer composition and distribution.

| Sample # | Elapsed Time | Residual Monomer Ratio N/M/H | Monomer Conversion N/M/H (%) | Calculated Polymer Composition (cumulative) | Cumulative Monomer Feed N/M/H |
|---|---|---|---|---|---|
| 11-0 | t = 0 | 12.7/74.6/12.7 | | | |
| 11-1 | 1.0 hr | NA | NA | NA | 14/38.1/14 |
| 11-2 | 2.0 hr | 26.5/44.9/28.6 | 9.0/17.2/1.7 | 21.0/74.9/4.0 | 22/41/22 |
| 11-3 | 3.5 hr | 29.9/39.6/30.4 | 13.1/21.6/11.7 | 23.2/56.2/20.6 | 30/44/30 |
| 11-4 | 5.0 hr | 29.9/41.4/28.7 | 37.0/40.7/39.7 | 27.1/43.8/29.1 | 30/44/30 |
| 11-5 | 22.3 hr | 24.8/60.2/14.9 | 97.5/95.9/98.5 | 29.0/41.8/29.3 | 30/44/30 |

NA = not available

The mixture was cooled, diluted with 18 mL methyl ethyl ketone, and added to heptane (1000 mL). The resulting solid was dissolved in THF (40 mL) and precipitated in heptane (1000 mL). Filtration, drying, and vacuum oven-drying (56° C., $N_2$ feed) for 48 hr gave 24.85 g of solid (85%).

Combined $^{13}C$ NMR and $^1H$ NMR analyses indicated the average composition as 2,3-NBFOHMA/MAMA/HADMA/MM=30%/36%/30%/4%. SEC analysis showed $M_w$=11,800, $M_n$=8,770, $M_w/M_n$=1.35.

UV analysis (THF, 1.00 g/liter) showed $A_{311.5}$=0.752.
MDSC: weak $T_g$ at 168° C.
TGA: onset of weight loss at ca. 170° C.

Example 12

Terpolymer of 2,3-NBFOHMA/MAMA/HADMA

A 3-neck flask fitted with reflux condenser and nitrogen gas inlet with adaptor to vacuum for de-gassing the reaction mixture before initiation, thermowell, and stir-bar was charged with trithiocarbonate RAFT agent $C_{12}H_{25}SC(S)SC(CH_3)(CN)CH_2CH_2CO_2CH_3$ (0.920 g, 2.20 mmol); monomer mixture, consisting of 2,3-NBFOHMA (10.80 g, 30 mmol), MAMA (9.84 g, 42 mmol), and HADMA (7.09 g, 30 mmol); methyl ethyl ketone (32 mL); V601 (164 mg, 0.7 mmol); and $NaHCO_3$ (0.145 g). The reactor was filled with nitrogen, and two more evacuation/fill cycles were performed. The temperature was increased (staged, but roughly linear ramp) to 67° C. over a 1.0 hr time interval. The reaction was maintained at 67° C. for 20 hr. Aliquots were withdrawn with time.

The reaction mixture was diluted with 50 mL MEK and filtered through a 5 micron membrane under $N_2$ pressure. Precipitation in heptane (1000 mL) provided uniform solid that was filtered and air-dried to give 23.9 g of solid. Vacuum drying gave 23.2 g. $^1H$ NMR showed no detectable monomers and no methacrylic acid functions.

MDSC: $T_g$ ca. 178° C. SEC Analyses:

| Sample | $M_w$ | $M_n$ | Polydispersity |
|---|---|---|---|
| 12-1 | 6,540 | 5,320 | 1.23 |
| 12-2 | 8,260 | 6,910 | 1.20 |
| 12-3 | 9,990 | 8,260 | 1.21 |
| 12-4 | 11,000 | 9,200 | 1.20 |
| precipitate | 11,000 | 9,230 | 1.19 |

UV analysis: THF, 1.00 g/liter; $A_{311.5}$=0.724.
$^{13}C$ NMR analysis showed 2,3-NBFOHMA/MAMA/HADMA=28.8/39.5/31.6.

Example 13

Tetrapolymer of 2,3-NBFOHMA/MAMA/PinMac/HADMA

A 3-neck flask fitted with reflux condenser and nitrogen gas inlet with adaptor to vacuum for de-gassing the reaction mixture before initiation, thermowell, and stir-bar was charged with trithiocarbonate RAFT agent $C_{12}H_{25}SC(S)SC(CH_3)(CN)CH_2CH_2CO_2CH_3$ (0.748 g, 1.79 mmol); monomer charge, consisting of 2,3-NBFOHMA (10.24 g, 28.46 mmol), MAMA (2.86 g, 12.2 mmol), PinMac (2.27 g, 12.2 mmol), and HADMA (6.72 g, 28.46 mmol); methyl ethyl ketone (26 mL); V601 (133 mg, 0.57 mmol); and $NaHCO_3$

| Sample # | Elapsed Time | Residual Monomer Ratio N/M/H | Monomer Conversion N/M/H | Calcd Polymer Composition (cumulative) |
|---|---|---|---|---|
| 12-1 | 2.0 hr | 29.7/43.7/26.6 | 45.1/42.4/50.7 | 29.0/38.3/32.7 |
| 12-2 | 3.0 hr | 29.8/45.5/24.7 | 64.5/61.3/70.6 | 29.2/38.9/31.9 |
| 12-3 | 5.0 hr | 28.8/51.8/19.5 | 85.7/81.6/90.3 | 29.5/39.4/31.1 |
| 12-4 | 20.0 hr | 22.8/64.7/12.4 | 96.3/92.5/98.0 | 29.7/40.0/30.2 |

(0.118 g). The reactor was filled with nitrogen, and two more evacuation/fill cycles were performed. The temperature was increased to 67° C. over a 1.0 hr time interval. The reaction was maintained at 67° C. for 21.4 hr. Aliquots were withdrawn with time to analyze residual monomer content and polymer composition.

| Sample # | Elapsed Time | Residual Monomer Ratio N/M/P/H | Monomer Conversion N/M/P/H | Calc'd Polymer Composition (cumulative) |
|---|---|---|---|---|
| 13-1 | 1.0 hr | 35.2/15.0/14.5/35.3 | 5.1/5.7/8.2/4.8 | 32.3/15.5/22.1/30.1 |
| 13-2 | 2.0 hr | 36.4/16.0/15.1/32.4 | 38.8/37.2/40.7/45.5 | 32.9/13.6/14.9/38.6 |
| 13-3 | 3.0 hr | 38.6/17.4/15.9/28.2 | 75.3/74.1/76.3/81.9 | 33.9/14.3/14.8/37.0 |
| 13-4 | 5.0 hr | 40.3/21.2/16.7/21.8 | 93.1/91.6/93.4/96.3 | 34.6/14.6/14.9/35.8 |
| 13-5 | 21.4 hr | 27.6/43.9/18.3/10.1 | 99.4/97.8/99.1/99.8 | 35.1/14.7/15.0/35.2 |

The mixture was diluted with 45 mL MEK, filtered through glass fiber paper, and precipitated in heptane (1400 mL) to provide a uniform solid that was filtered and air-dried to give 22.67 g of solid. The product was oven-dried for 2 days (56° C./vacuum with $N_2$ purge) to give 20.98 g (91.9% of theory). $^1$H NMR showed no detectable monomers, no methacrylic acid.

MDSC: $T_g$ ca. 175° C. SEC Analyses:

| Sample # | $M_w$ | $M_n$ | Polydispersity |
|---|---|---|---|
| 13-1 | 3,250 | 2,480 | 1.31 |
| 13-2 | 6,320 | 5,060 | 1.25 |
| 13-3 | 9,250 | 7,830 | 1.18 |
| 13-4 | 10,800 | 9,250 | 1.17 |
| 13-5 | 11,500 | 9,830 | 1.17 |
| precipitate | 11,600 | 9,840 | 1.18 |

UV analysis: THF, 1.00 g/liter; $A_{311.0}$=0.656.

$^{13}$C NMR was consistent with 2,3-NBFOHMA/MAMA/PinMac/HADMA=37.3/13.6/12.4136.7.

We claim:

1. An acrylic polymer having a polydispersity in the range of 1.05 to 1.3, said polymer consisting essentially of:
   a repeat unit derived from an acrylic monomer selected from the group consisting of acrylate and methacrylate esters,
   wherein at least one of said repeat units has a functional group selected from the group consisting of fluoroalcohol and protected fluoroalcohol groups, wherein the mole percent of said repeat units having the functional groups is from 28.8 to 75.4 mole percent based on the moles of repeat units of said acrylic polymer; and
   wherein said polymer has a weight average molecular weight of 14,600 or less from 3,250 to 14,600.

2. The acrylic polymer of claim 1, wherein the acrylic monomer is $CH_2$=CR'CO$_2$R" and
   R' is H, F, an alkyl group of 1 to 5 carbon atoms, or a fluoroalkyl group of 1 to 5 carbon atoms; and
   R" is a $C_1$-$C_{20}$ acyclic aliphatic group cyclic $C_5$-$C_{50}$ or a polycyclic $C_7$-$C_{50}$ alkyl group, optionally containing at least one hydroxy functional group, or a functional group of the formula —C($R^1$)($R^2$)—[C($R^3$)($R^4$)]m-C($R^5$)($R^6$)—OH, wherein m=0, 1, 2, 3, 4 or 5;
   $R^1$ and $R^2$ are independently $C_1$-$C_6$ alkyl, $C_1$-$C_6$ alkyl substituted with an ether oxygen, or $R^1$ and $R^2$ taken together form a 3- to 8-membered ring, optionally substituted with an ether oxygen, provided that the carbon attached to $R^1$ and $R^2$ is not at a bridgehead position;
   $R^3$ and $R^4$ are independently H, $C_1$-$C_6$ alkyl, $C_1$-$C_6$ alkyl substituted with an ether oxygen, or $R^3$ and $R^4$ taken together form a 3- to 8-membered ring, optionally substituted with an ether oxygen;
   $R^5$ and $R^6$ are independently H, $C_1$-$C_6$ alkyl, $C_1$-$C_6$ alkyl substituted with an ether oxygen, or $R^5$ and $R^6$ taken together form a 3- to 8-membered ring, optionally substituted with an ether oxygen; or
   $R^1$ and $R^5$ taken together with —[C($R^3$)($R^4$)]$_m$— form a 4- to 8-membered ring, provided that the carbon attached to $R^1$ and $R^2$ is not at a bridgehead position.

3. The acrylic polymer of claim 1, wherein the acrylic monomer is selected from the group consisting of PinMAc (2-methyl-2-propenoic acid, 2-hydroxy-1,1,2-trimethylpropyl ester); PinAc; 2-methyl-2-adamantyl (meth)acrylate; 2-ethyl-2-adamantyl-(meth)acrylate; 2-propyl-2-adamantyl-(meth)acrylate; 2-(1-adamantyl)-2-propyl(meth)acrylate; α-(γ-butyrolactone)-(meth)acrylate; β-(γ-butyrolactone)-(meth)acrylate; 3-hydroxy-1-adamantyl-(meth)acrylate; 8-methyltricyclo-[5.2.1]decan-8-yl-(meth)acrylate; 8-ethyltricyclo[5.2.1]decan-8-yl-(meth)acrylate; 2-(4-methoxybutyl)-2-adamantyl-(meth)acrylate; mevalonic lactone-(meth)acrylate; PinAc; PinMAc; 4-hydroxy-1-methylcyclohexyl-(meth)acrylate; 1-methylcyclopentyl-(meth)acrylate; 1-ethylcyclopentyl-(meth)acrylate; 3-(2,2-bis(trifluoromethyl)-2-hydroxyethyl)-endo-2-(2-methylpropenoyl)-bicyclo[2.2.1]heptane; 3-(2,2-bis(trifluoromethyl)-2-hydroxyethyl)-endo-2-(propenoyl)-bicyclo[2.2.1]-heptane; and 5-(meth)acryloyloxy-2,6-norbornanecarbolactone.

4. The acrylic polymer of claim 1, wherein the functional group is a fluoroalcohol functional group having the structure:

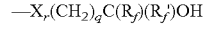

wherein $R_f$ and $R_f'$ are the same or different fluoroalkyl groups of from 1 to 10 carbon atoms, or taken together are $(CF_2)_n$; n is an integer from 2 to 10; X is selected from the group consisting of S, O, N, and P; and q=0 and r=0; or q=1 and r=0 or 1.

5. The acrylic polymer of claim 1, wherein the functional group is a protected fluoroalcohol having the structure:

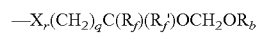

wherein $R_f$ and $R_f'$ are the same or different fluoroalkyl groups of from 1 to 10 carbon atoms, or taken together are $(CF_2)_n$; n is an integer from 2 to 10; X is selected from the group consisting of S, O, N, and P;
q=0 and r=0; or q=1 and r=0 or 1; and
$R_b$ is $C_1$-$C_{11}$ alkyl.

* * * * *